(12) United States Patent
Rotter et al.

(10) Patent No.: US 8,668,290 B2
(45) Date of Patent: *Mar. 11, 2014

(54) RACK AND PINION REFRIGERATOR STORAGE SYSTEM

(75) Inventors: Chad J. Rotter, Amana, IA (US); Lester J. Ott, Swisher, IA (US); Steven G. Herndon, Cedar Rapids, IA (US)

(73) Assignee: Whirlpool Corporation, Benton Harbor, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/489,485

(22) Filed: Jun. 6, 2012

(65) Prior Publication Data

US 2012/0242212 A1 Sep. 27, 2012

Related U.S. Application Data

(60) Continuation of application No. 13/196,282, filed on Aug. 2, 2011, which is a division of application No. 12/135,380, filed on Jun. 9, 2008, now Pat. No. 7,997,667.

(51) Int. Cl.
*A47B 96/04* (2006.01)

(52) U.S. Cl.
USPC ........ 312/402; 312/404; 312/334.7; 312/311; 312/350; 312/352

(58) Field of Classification Search
USPC ........... 312/402, 404, 331, 334.1, 334.7, 311, 312/350
See application file for complete search history.

(56) References Cited

U.S. PATENT DOCUMENTS

| 6,971,730 | B2 * | 12/2005 | Koons | 312/404 |
|---|---|---|---|---|
| 7,594,707 | B2 * | 9/2009 | Kunkle et al. | 312/402 |
| 7,712,852 | B2 * | 5/2010 | Choi et al. | 312/402 |
| 7,997,667 | B2 * | 8/2011 | Rotter et al. | 312/402 |
| 8,147,013 | B2 * | 4/2012 | Park | 312/402 |
| 8,157,339 | B2 * | 4/2012 | Park et al. | 312/404 |
| 2005/0160854 | A1 * | 7/2005 | Rotter | 74/422 |
| 2006/0250059 | A1 * | 11/2006 | Lemm | 312/331 |
| 2009/0261698 | A1 * | 10/2009 | Cabal Velarde et al. | 312/334.8 |
| 2009/0322196 | A1 * | 12/2009 | Park | 312/404 |
| 2010/0283365 | A1 * | 11/2010 | Chen | 312/334.4 |
| 2011/0050065 | A1 * | 3/2011 | Lee et al. | 312/402 |
| 2012/0125035 | A1 * | 5/2012 | Chellappan et al. | 62/340 |

FOREIGN PATENT DOCUMENTS

CN 1959315 A * 5/2007

* cited by examiner

*Primary Examiner* — Daniel Rohrhoff

(57) ABSTRACT

A rack and pinion storage system for use in a refrigerator compartment defined by a liner includes a pair of supports attached to opposing sidewalls of the liner. First and second gear covers snap-fittingly connect first and second gear wheels to respective first and second mounting brackets extending from a storage basket, such that the gear wheels are rotatably connected to the storage basket and have equal rotational and linear motion along the respective supports. Retaining bars extending from the storage basket are held within channels defined between the bottom walls of the supports and top walls of opposing telescoping slide assemblies used to movably support a door of the compartment. Tabs extending from the supports limit the sliding movement of the storage basket. A removable divider connects to the storage basket, sectioning the basket into multiple storage compartments.

18 Claims, 5 Drawing Sheets

RACK AND PINION REFRIGERATOR STORAGE SYSTEM

CROSS-REFERENCE TO RELATED APPLICATIONS

This application represents a continuation application of U.S. application Ser. No. 13/196,292, filed Aug. 2, 2011, which application is a divisional of U.S. application Ser. No. 12/135,380, filed Jun. 9, 2008, now U.S. Pat. No. 7,997,667.

BACKGROUND OF THE INVENTION

1. Field of the Invention

The present invention relates to the art of refrigerators and, more specifically, to a rack and pinion storage system for a drawer assembly of a refrigerator.

2. Discussion of the Related Art

Pullout drawers in refrigerator cabinets, and in particular bottom mounted freezer drawers in which the freezer compartment is located at the bottom of the refrigerator while the fresh food compartment is located at the top of the refrigerator, are often used to increase versatility of storing a wide range of food items, and increasing the accessibility of items stored in the lower portion of the refrigerator cabinet. To this end, in commercially available bottom mounted freezers, a large freezer drawer or basket is provided in connection with or in place of a hinged or swinging door. These bottom mounted freezer drawers are typically mounted on slides or glides fastened to the sidewalls of the inner liner of the refrigerator cabinet and telescopically extend horizontally, outwardly of the refrigerator. Unfortunately, these slides extend at different rates when the large drawer is opened and closed, particularly when the horizontal force, i.e., the consumer pushing or pulling on the drawer or basket, is not centered. The effect of the different rates of extension creates a "wobble" as the drawer or basket is extended and inserted. This drawer rack or wobble typically occurs when the velocity of the drawer and glide assembly varies with position along the face of the drawer as it is extended or inserted.

A further problem with presently available systems is that it is difficult to ensure identical, or near identical, placement relative to the refrigerator cabinet face of left and right drawer components. Without proper component placement, the drawer may not completely close, resulting in the failure to create an effective seal which allows air to permeate into or out of the drawer. The inability of the drawer to completely close creates an inefficient system, making it difficult to regulate temperatures, humidity, and other factors within the drawer.

Attempts have been made in drawer systems to overcome wobble or racking problems. For instance, anti-rack systems have been developed for drawers and drawer glides in which a shaft having a gear wheel mounted on each side is used for engaging associated racks. Though such systems prevent wobble, these attempts have not prevented the drawer from assuming a racked condition resulting from the opening force or food load center of mass occurring significantly away from the drawer's center. Likewise, no simple means of aligning, during initial assembly, left and right gear wheels to associated rack gears of a drawer employing a rack and pinion system has been available. As a result, if the drawer, and in particular the rack and pinion system, becomes misaligned, no means exists for the correction of the misaligned drawer apart from complete disassembly and removal of the drawer from the cabinet. This task becomes particularly difficult when the drawer is filled with food or other stored items.

Complex mechanisms involving the resetting of misaligned slide pairs in a drawer suspension system have been developed. Such systems require the removal, reinsertion and moving of the drawer in and out from the cabinet to reset the misaligned drawer. Due to the removal and reinsertion of the drawer, as well as the inward and outward movement required to reset the misaligned drawer, these systems do not provide much improvement, as the drawer must still be removed, and a significant amount of effort is required of the drawer operator to realign the drawer.

Other systems exist that involve a single displaceable gear tooth provided on the end of a rack gear for enabling meshing with a single pinion that approaches from beyond the end of the rack. The use of a single rack and pinion, however, does not provide a stable means of securing the drawer, as a minor amount of lateral force or movement of the drawer will cause misalignment of the drawer, as well as the rack and pinion, causing wobble, or resulting in jamming of the drawer.

Therefore, there exists a need in the art for a simple and easily installed refrigerator drawer system having a stable means for sliding the drawer into and out of a refrigerator cabinet.

SUMMARY OF THE INVENTION

The present invention is directed to a rack and pinion storage system for a refrigerator compartment. In general, the system includes a storage basket, a pair of supports mounted on opposing sidewalls of the refrigerator compartment, a gear assembly, and a pair of gear covers. The gear assembly comprises two gear wheels attached at their respective hubs by an axle. The gear covers are adapted to snap-fittingly engage respective retainers or mounting brackets extending from opposing sides of the storage basket.

In use, the gear covers are partially attached to the respective retainers and the gear wheels are connected by the axle extending through the gear covers and retainers. The storage basket can then be angled such that first and second retaining bars extending from the basket are hooked under tabs extending from the respective supports. First and second retaining bars extending from the bottom of the storage basket fit within a channel defined by the top walls of telescoping slide assemblies and the supports. The gear wheels are then aligned upon rack gears located on respective supports, and the gear covers are snapped into full engagement with the retainers. With this configuration, the gear wheels are rotatably connected to the storage basket and have equal rotational and linear motion along the rack gears when the storage basket is slid into and out of the refrigerator compartment. In this fully assembled configuration, the gear covers lock the gear assembly to the basket, and the tabs engage the retaining bar to prevent the storage basket from being removed from the refrigerator compartment. Optionally, a removable basket divider may be utilized to partition the storage basket into multiple storage units.

Additional objects, features and advantages of the present invention will become more readily apparent from the following detailed description of a preferred embodiment when taken in conjunction with the drawings wherein like reference numerals refer to corresponding parts in the several views.

DETAILED DESCRIPTION OF PREFERRED EMBODIMENT

Figure 1:
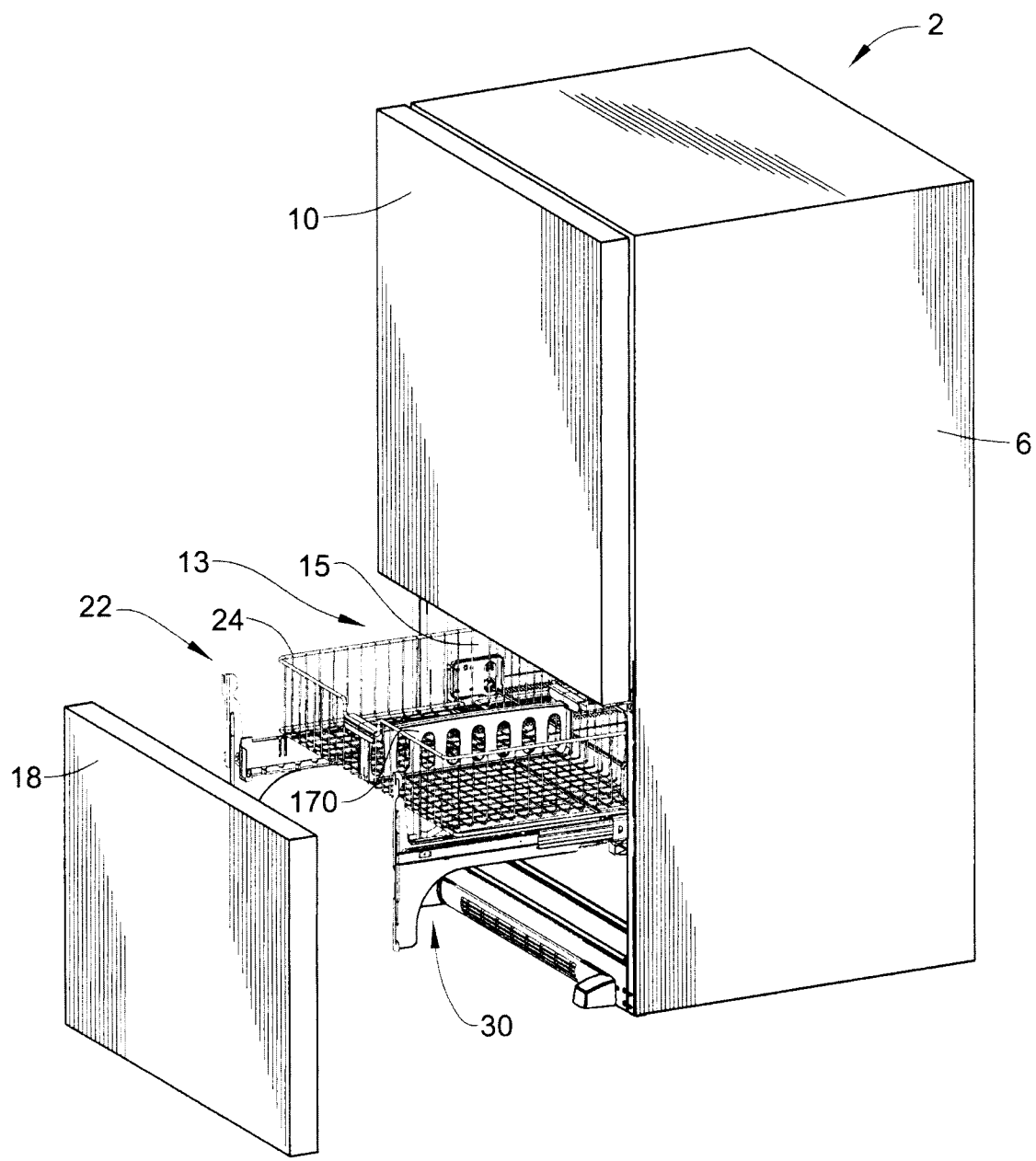
FIG. 1 is a partial exploded view of a bottom mount style refrigerator incorporating the rack and pinion storage system of the invention.

With initial reference to FIG. 1, a refrigerator incorporating the invention is generally indicated at 2. Refrigerator 2 includes a cabinet shell 6 to which is attached a fresh food compartment door 10. At this point, it should be readily recognized that refrigerator 2 constitutes a bottom mount style refrigerator wherein fresh food compartment door 10 is adapted to seal off an upper fresh food compartment defined within cabinet shell 6. In a manner known in the art, fresh food compartment door 10 is preferably, pivotally mounted about a vertical axis to cabinet shell 6 through upper and lower hinges (not shown). Refrigerator 2 also includes a lower freezer compartment 13 which is defined by a liner having opposing sidewalls 15. Freezer compartment 13 is adapted to be sealed by means of a freezer door 18. In accordance with the present invention, freezer door 18 is adapted to slide towards and away from cabinet shell 6, in part, through the use of a stabilizer system indicated at 22, which is set forth in more detail in U.S. Patent Application Publication No. 2005/0160854, herein incorporated by reference. Mounted adjacent stabilizer system 22 is a rack and pinion storage system indicated at 24.

Figure 2:
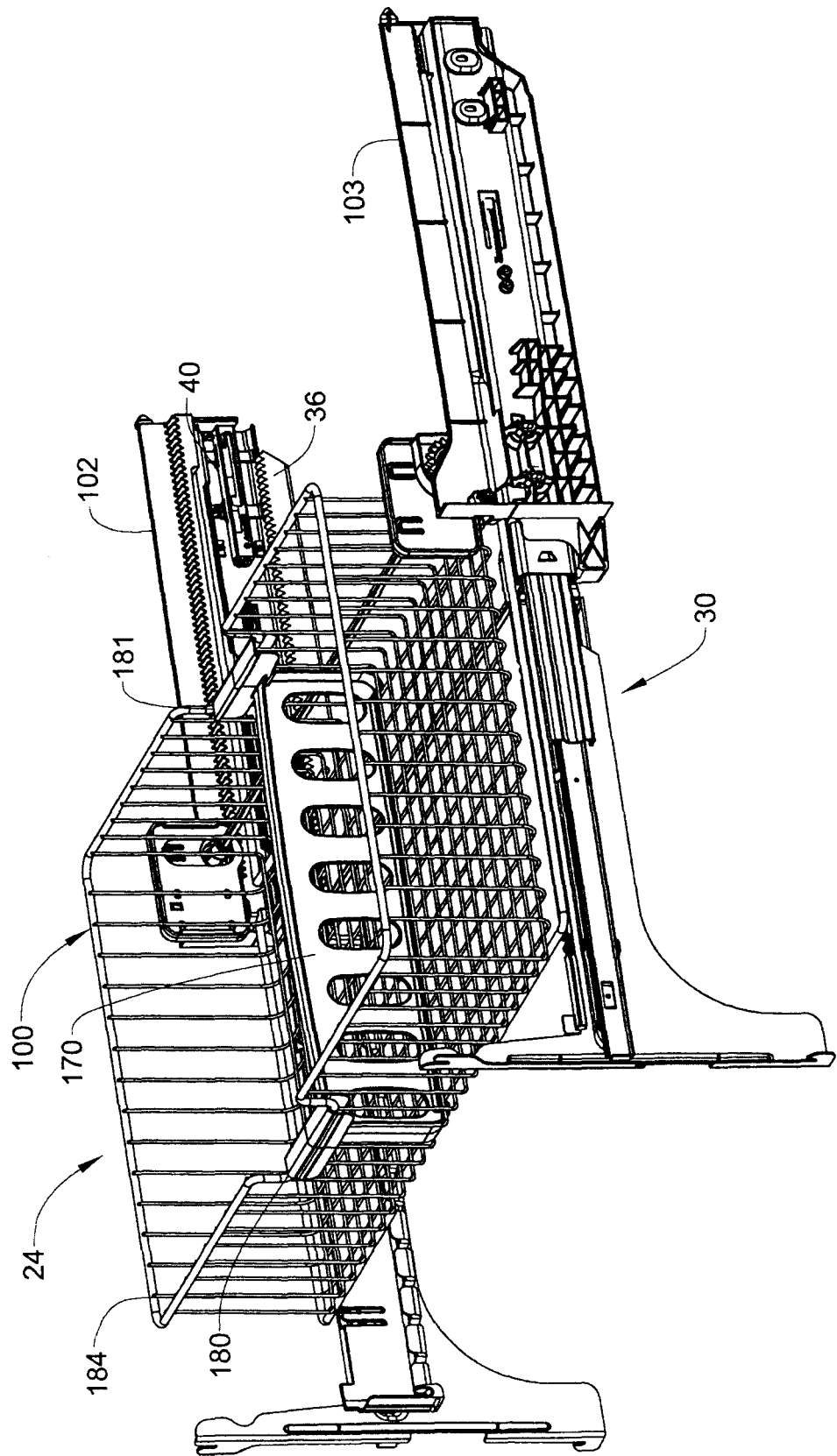
FIG. 2 is an enlarged view of a drawer stabilizer system and the rack and pinion storage system of FIG. 1.

With reference to FIG. 2, stabilizer system 22 generally includes a pair of telescoping slide assemblies 30 movably mounted relative to liner 15. Slide assemblies 30 include bottom rack gears 36, and gear wheels linked by a transverse axle (not shown) for the combined rotation of the gear wheels on bottom gears 36. A lower drawer (not shown), may be fastened to the axle and/or the slide assemblies 30 for sliding movement of the lower drawer into and out of freezer compartment 13 with door 18. Rack and pinion storage system 24 of the present invention is mounted adjacent respective top walls 40 of slide assemblies 30 as will be discussed more fully below.

Figure 3:
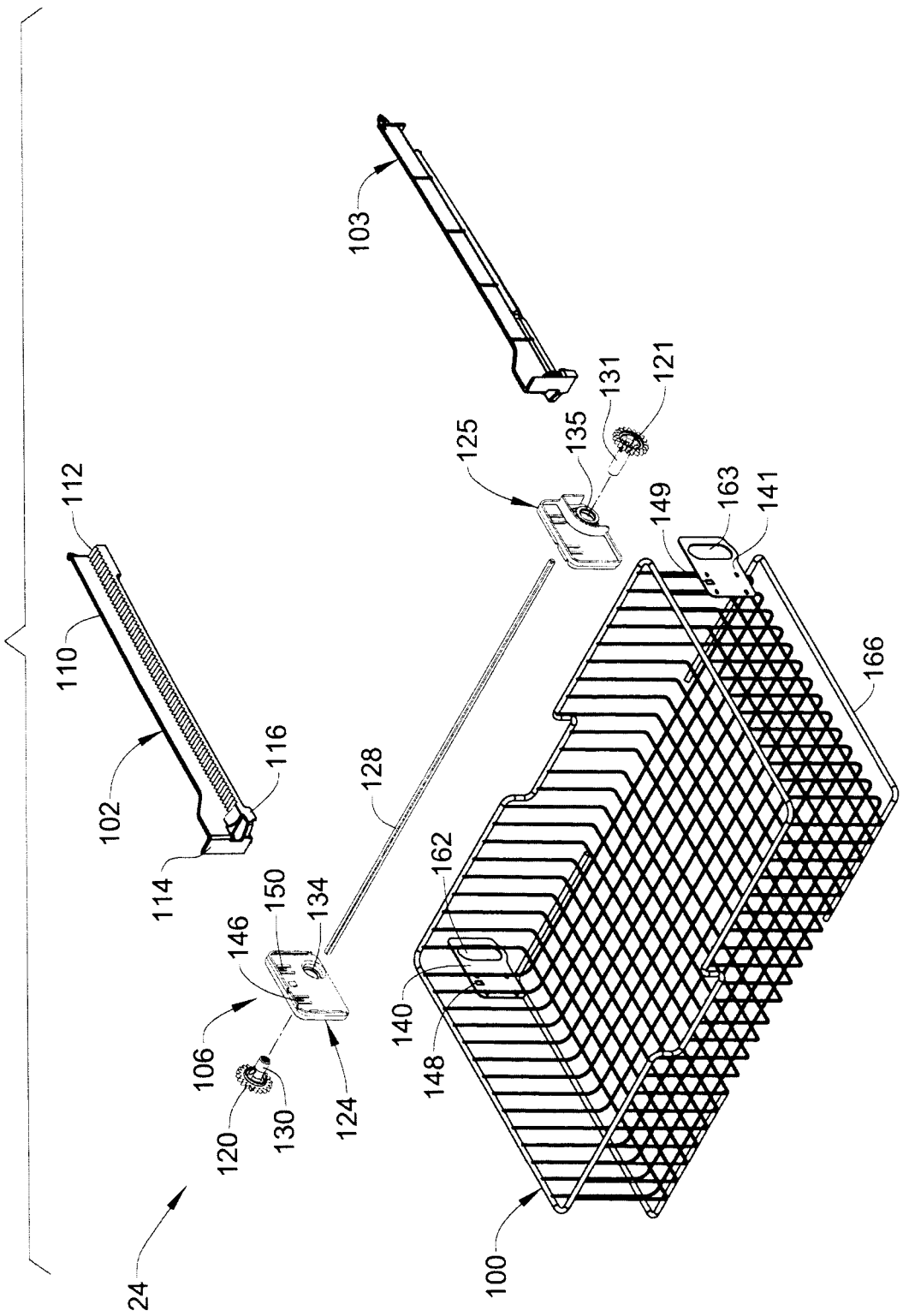
FIG. 3 is an exploded view of the rack and pinion storage system of FIG. 2.

With reference to FIG. 3, rack and pinion storage system 24 of the present invention includes a storage unit or basket 100, first and second supports 102 and 103 and a gear assembly 106. In general, first and second supports 102 and 103 comprise respective sidewall portions 110, rack gears 112, front wall portions 114 and tabs 116 extending downward adjacent a front end of rack gears 112. Gear assembly 106 includes a pair of gear wheels 120 and 121 in operable, rotatable communication with respective rack gears 112. Gear assembly 106 further comprises gear mounting covers 124 and 125 and an axle 128 linking gear wheels 120 and 121. Hubs 130 and 131 of respective gear wheels 120 and 121 are adapted to be inserted through respective apertures 134 and 135 of gear covers 124 and 125 and drivingly interconnected by axle 128. In the embodiment shown, axle 128 extends horizontally within freezer compartment 13. When linked, gear wheels 120 and 121 co-rotate, in unison, relative to gear covers 124 and 125.

Figure 4:
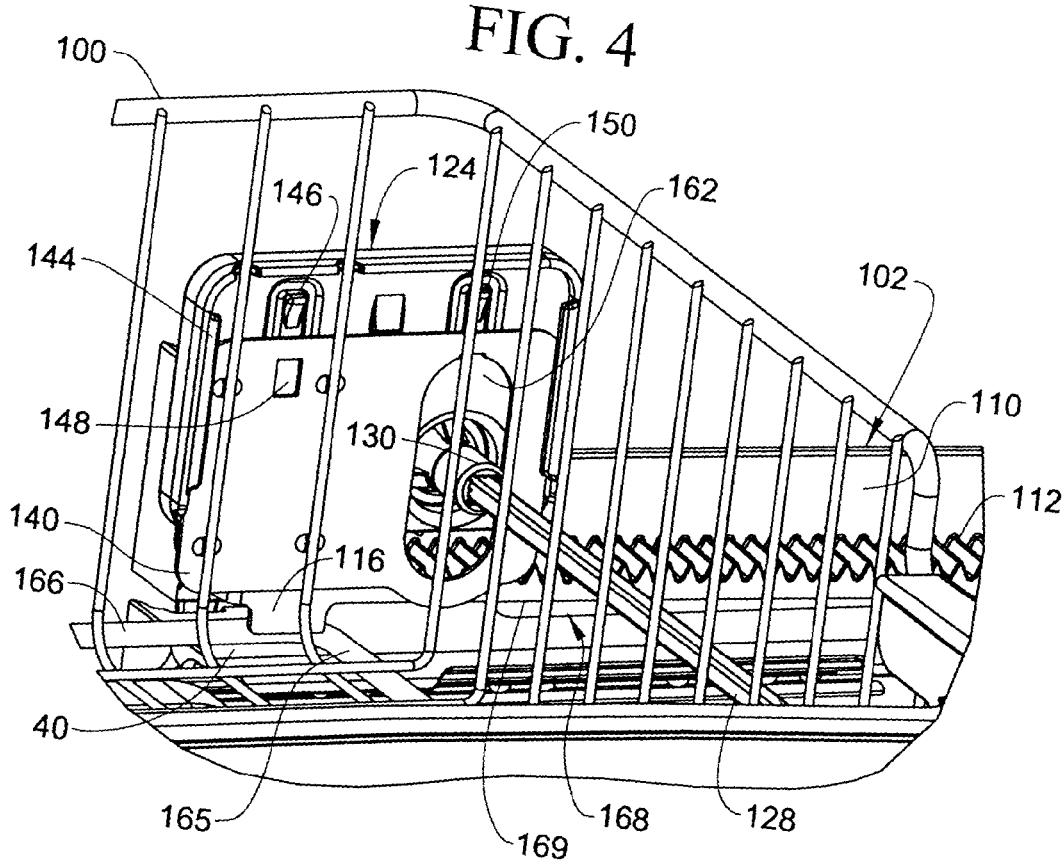
FIG. 4 is a partial perspective view of a partially connected gear assembly of the present invention.

As best seen in FIGS. 3 and 4, gear covers 124 and 125 are adapted to slidingly and snap-fittingly attach to respective retainers or mounting brackets 140 and 141 extending from opposite sides of basket 100. More specifically, gear covers 124 and 125 each include side arms 144 adapted to slide over and connect covers 124 and 125 to respective retainers 140 and 141, with a first projection 146 on each cover 124, 125 being adapted to snap-fittingly extending into a respective cut-out 148, 149 in retainers 140 and 141. Additionally, gear covers 124 and 125 each include a second projection 150 adapted to extend into respective gear wheel cut-outs 162 and 163.

Figure 5:
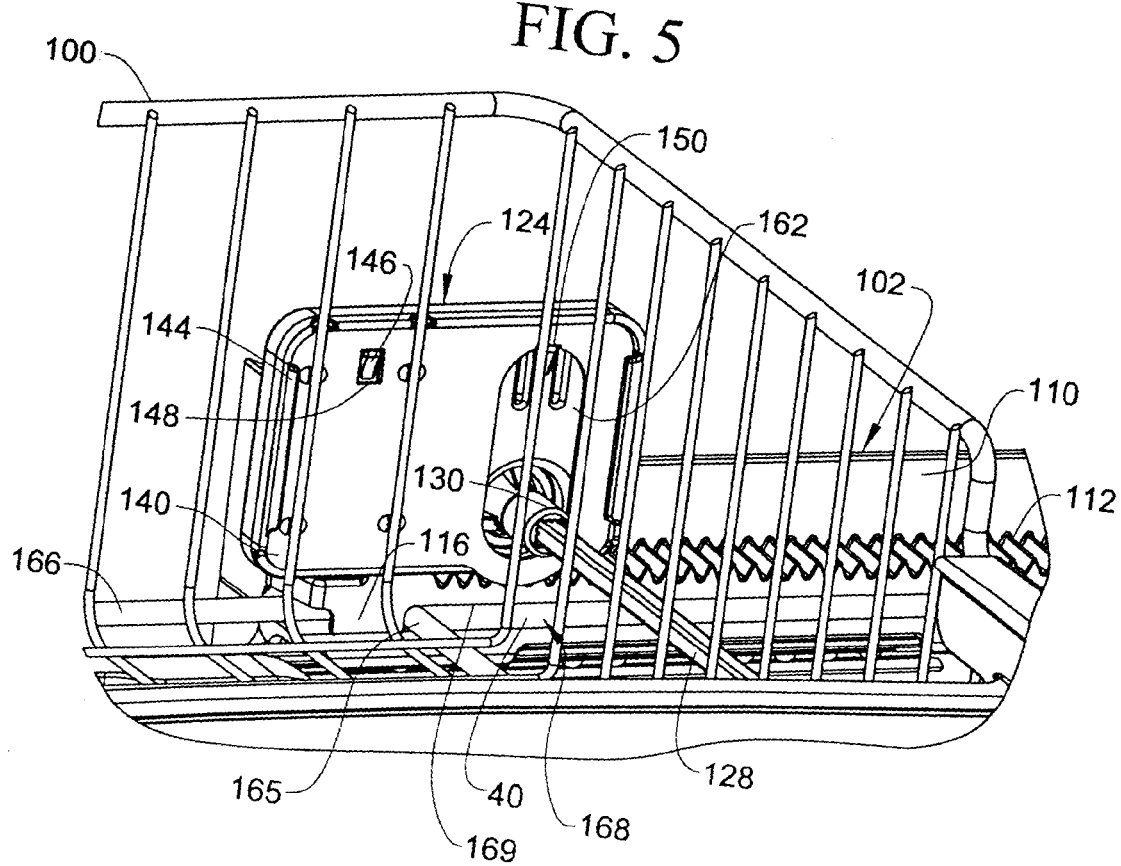
FIG. 5 is a partial perspective view of a fully connected gear assembly of the present invention.
Figure 6:
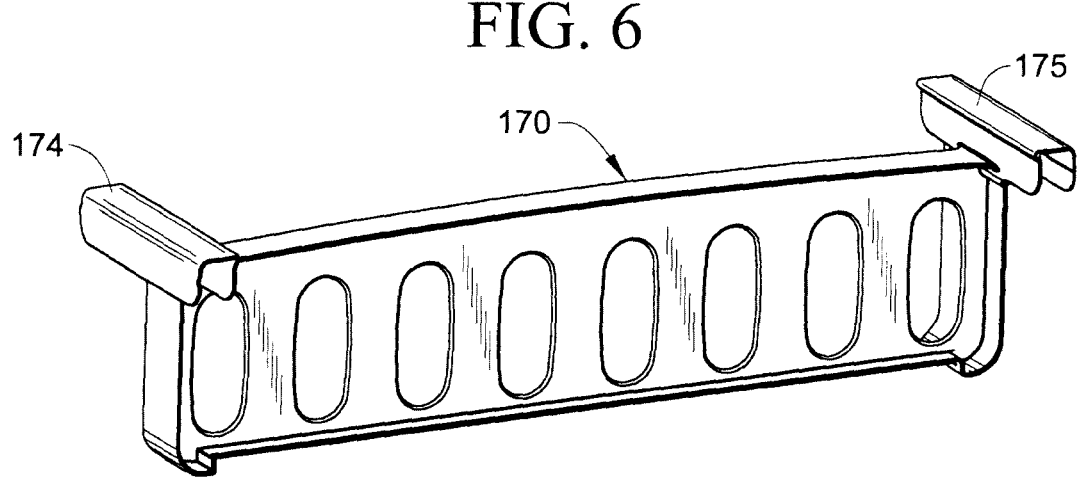
FIG. 6 is a perspective view of a first basket divider of the present invention.
Figure 7:
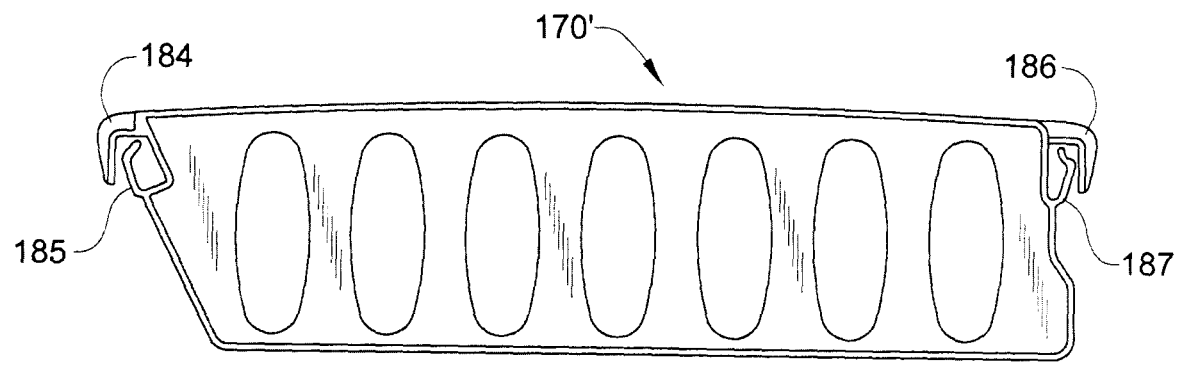
FIG. 7 is a perspective view of a second basket divider of the present invention.

The manner in which the rack and pinion storage system of the present invention is assembled for use will now be discussed with reference to FIGS. 3-5. Initially, gear assembly 106 is connected with gear covers 124 and 125 and retainers 140 and 141. More specifically, side arms 144 of cover 124 are placed partially over retainer 140 such that cover 124 is located adjacent the inside surface of retainer 140. Hub 130 of gear wheel 120 is inserted through aperture 134 of cover 124 and gear wheel cut-out 162 of retainer 140 and axle 128 is attached to hub 130 through aperture 134 and gear wheel cut-out 162. The same procedure is repeated with respect to gear wheel 121, cover 125 and retainer 141. In this manner, gear assembly 106 is attached to basket 100, via axle 128 and covers 124 and 125. At this point, to install basket 100 on first and second supports 102 and 103, basket 100 is tilted such that crossbars 165 of lower retaining bars 166 extending laterally, partially across from opposing sides of basket 100 can be slid under tabs 116 projecting from first and second supports 102 and 103. Although shown as two bars, it should be understood that a single retaining bar 166 extending the width of basket 100 may be utilized.

Once retaining bar 166 is located beyond tabs 116, covers 124 and 125 are shifted further downward and snapped to respective retainers 140 and 141 to secure gear assembly 106 in alignment with respective rack gears 112. More specifically, basket 100 is aligned against tabs 116 and cover 124 is pushed down over retainer 140 such that side arms 144 fully engage retainer 140 and projections 146 and 150 engage respective cut-outs 148 and 162 in a locking manner. Simultaneously or sequentially, cover 125 is pushed down over retainer 141 in a similar manner. The engagement of covers 124 and 125 with retainers 140 and 141 cause gear wheels 120 and 121 to engage respective rack gears 112 of first and second supports 102 and 103. As depicted in FIG. 5, once covers 124 and 125 are snapped to retainers 140 and 141, basket 100 can no longer be tilted to any significant extent and tabs 116 engage retaining bars 166 to prevent basket 100 from being removed from freezer compartment 13.

As should be understood from the above description of system 24, basket 100 is supported by top walls 40 of telescoping slide assemblies 30 when in both of the opened and closed positions. At the same time, gear wheels 120 and 121 are engaged with rack rears 112 such that, when basket 100 is slid to an open position, the teeth on gear wheels 120 and 121 engage corresponding rack gears 112 which are rigidly fastened to liner 15, providing equal rotational and linear motion of gear wheels 120 and 121 along respective rack gears 112. Retaining bars 166 slide within channels 168 created between the top walls 40 of telescoping slide assemblies 30 and bottom walls 169 of first and second supports 102 and 103, as best seen in FIGS. 4 and 5. Thus, system 24 provides a permanent drawer system having smooth travel into and out of freezer compartment 13 without the need for ball bearing drawer slides or the like. Advantageously, as one pulls or pushes basket 100, all points of the basket assembly will have the approximate same linear velocity, disallowing the basket to skew rotationally in a horizontal plane. Additionally, system 24 provides a permanent storage space, thus limiting the continuous storage volume in freezer compartment 13 and allowing more control over the maximum storage capacity for safety purposes.

In an additional aspect of the present invention, rack and pinion storage system 24 preferably includes a basket divider, as depicted in FIGS. 1, 2, 6 and 7, for sectioning basket 100 into multiple storage compartments. In a first embodiment, a basket divider 170 includes first and second longitudinally extending arms 174 and 175 adapted to fit over opposing wire end portions 180, 181 of basket 100. In an alternative embodiment, a basket divider 170' includes a first downwardly extending arm 184 adjacent an upwardly extending snap-finger 185 and an opposing second downwardly extending arm 186 adjacent an upwardly extending snap-finger 187. In use, divider 170' snaps over opposing wire end portions 180 and 181, with wire end portions 180 and 181 being retained by snap fingers 185 and 187. In one preferred embodiment, opposing end portions 180 and 181 are lower than the topmost portion of a basket wall 184, providing a niche within which dividers 170 and 170' may be retained.

Although described with reference to preferred embodiments of the invention, it should be readily understood that various changes and/or modifications can be made to the invention without departing from the spirit thereof. For instance, although shown in conjunction with a bottom-mount freezer drawer, it should be understood that the above system could be utilized within other known refrigerated compartment arrangements. In general, the invention is only intended to be limited by the scope of the following claims.

What is claimed is:

1. A refrigerator comprising:
   a refrigerated compartment defined by a liner having opposing side walls;
   a storage unit provided within the refrigerated compartment, wherein the storage unit is coupled to the liner with a rack and pinion system comprising:
   opposing first and second mounting brackets coupled to the storage unit;
   first and second supports including respective first and second rack gears, said first and second supports being mounted to the opposing side walls of the liner, wherein the first and second supports include respective downwardly projecting tabs for limiting movement of the storage unit from the refrigerated compartment;
   first and second gear wheels interconnected by an axle for co-rotation, said first and second gear wheels being engaged with the first and second rack gears, respectively, and;
   first and second gear cover members connecting the first and second gear wheels to the storage unit through the first and second mounting brackets while supporting the first and second gear wheels for rotation relative to the storage unit, said first and second gear cover members being detachably connected to the first and second mounting brackets,
   wherein the first and second gear wheels exhibit equal rotational and linear motion along the respective first and second rack gears upon shifting of the storage unit into and out of the refrigerated compartment.

2. The refrigerator of claim 1, further comprising a divider sectioning the storage unit into multiple storage compartments.

3. The refrigerator of claim 2, wherein the divider comprises first and second opposing longitudinally extending arms that removably fit over respective opposing end portions of the storage unit such that the divider divides an interior of said storage unit into first and second storage compartments.

4. A refrigerator comprising:
   a refrigerated compartment defined by a liner having opposing side walls;
   a storage unit provided within the refrigerated compartment, wherein the storage unit is coupled to the liner with a rack and pinion system comprising:
   opposing first and second mounting brackets coupled to the storage unit;
   first and second supports including respective first and second rack gears, said first and second supports being mounted to the opposing side walls of the liner;
   first and second gear wheels interconnected by an axle for co-rotation, said first and second gear wheels being engaged with the first and second rack gears, respectively; and
   first and second gear cover members connecting the first and second gear wheels to the storage unit through the first and second mounting brackets while supporting the first and second gear wheels for rotation relative to the storage unit, said first and second gear cover members being detachably connected to the first and second mounting brackets,
   wherein each of the first and second gear cover members extend about and around gear portions of the first and second gear wheels respectively; and
   wherein the first and second gear wheels exhibit equal rotational and linear motion along the respective first and second rack gears upon shifting of the storage unit into and out of the refrigerated compartment.

5. The refrigerator of claim 4, further comprising a divider sectioning the storage unit into multiple storage compartments.

6. The refrigerator of claim 5, wherein the divider comprises first and second opposing longitudinally extending arms that removably fit over respective opposing end portions of the storage unit such that the divider divides an interior of said storage unit into first and second storage compartments.

7. The refrigerator of claim 4, wherein the first and second supports include respective downwardly projecting tabs for limiting movement of the storage unit from the refrigerated compartment.

8. The refrigerator of claim 4, wherein the first and second gear cover members are snap-fittingly connected to the first and second mounting brackets.

9. The refrigerator of claim 8, wherein the first and second gear cover members are snap-fittingly connected to the first and second mounting brackets with resilient projections extending into respective cut-out portions.

10. The refrigerator of claim 9, wherein the projections extend from the first and second gear cover members and extend into cut-out portions on the first and second mounting brackets.

11. A refrigerator comprising:
    a refrigerated compartment defined by a liner having opposing walls; and
    a rack and pinion system coupling a storage system including a storage unit and opposing first and second mounting brackets to the liner, the rack and pinion system comprising:
    first and second supports including respective first and second rack gears, said first and second supports being mounted to the opposing side walls of the liner;

first and second gear wheels interconnected by an axle for co-rotation, said first and second gear wheels being engaged with the first and second rack gears, respectively;

first and second gear cover members connecting the first and second gear wheels to the storage unit through the first and second mounting brackets while supporting the first and second gear wheels for rotation relative to the storage unit, said first and second gear cover members being detachably connected to the first and second mounting brackets;

wherein the first and second gear wheels exhibit equal rotational and linear motion along the respective first and second rack gears upon shifting of the storage unit into and out of the refrigerated compartment, and a divider sectioning the storage unit into multiple storage compartments.

12. The refrigerator of claim 11, wherein the divider comprises first and second opposing longitudinally extending arms that removably fit over respective opposing end portions of the storage unit such that the divider divides an interior of said storage unit into first and second storage compartments.

13. The refrigerator of claim 11, wherein the first and second supports include respective downwardly projecting tabs for limiting movement of the storage unit from the refrigerated compartment.

14. A refrigerator comprising:
a refrigerated compartment defined by a liner having opposing walls;
a storage unit including opposing first and second mounting brackets and at least one retaining bar extending along a bottom portion of the storage unit;
a rack and pinion system coupling the storage unit to the liner, the rack and pinion system comprising:
first and second supports including respective first and second rack gears, said first and second supports being mounted to the opposing side walls of the liner;
first and second gear wheels interconnected by an axle for co-rotation, said first and second gear wheels being engaged with the first and second rack gears, respectively;
wherein the first and second rotatable gear wheels are connected to the storage unit through the first and second mounting brackets while supporting the first and second gear wheels for rotation relative to the storage unit; and
wherein the first and second gear wheels exhibit equal rotational and linear motion along the respective first and second rack gears upon shifting of the storage unit into and out of the refrigerated compartment; and
a bottom slide assembly attached to the liner below the first and second supports and supporting a door for movement relative to the liner, wherein the at least one retaining bar is supported upon and glides along a top wall portion of the bottom slide assembly upon shifting of the storage unit into and out of the refrigerated compartment.

15. The refrigerator of claim 14, wherein the first and second supports include respective downwardly projecting tabs for limiting movement of the storage unit from the refrigerated compartment.

16. The refrigerator of claim 14, further comprising a divider sectioning the storage unit into multiple storage compartments.

17. The refrigerator of claim 16, wherein the divider comprises first and second opposing longitudinally extending arms that removably fit over respective opposing end portions of the storage unit such that the divider divides an interior of said storage unit into first and second storage compartments.

18. The refrigerator of claim 17, wherein the first and second supports include respective downwardly projecting tabs for limiting movement of the storage unit from the refrigerated compartment.

* * * * *